(12) United States Patent
Myntti

(10) Patent No.: US 11,273,175 B2
(45) Date of Patent: Mar. 15, 2022

(54) METHOD FOR TREATING FIBRILLAR COLLAGENOUS CONDITIONS

(71) Applicant: Next Science IP Holdings Pty Ltd, Chatswood (AU)

(72) Inventor: Matthew F. Myntti, St. Augustine, FL (US)

(73) Assignee: Next Science IP Holdings Pty Ltd, Chatswood (AU)

(*) Notice: Subject to any disclaimer, the term of this patent is extended or adjusted under 35 U.S.C. 154(b) by 15 days.

(21) Appl. No.: 16/626,194

(22) PCT Filed: Jun. 23, 2018

(86) PCT No.: PCT/US2018/039177
§ 371 (c)(1),
(2) Date: Dec. 23, 2019

(87) PCT Pub. No.: WO2019/005643
PCT Pub. Date: Jan. 3, 2019

(65) Prior Publication Data
US 2020/0113936 A1    Apr. 16, 2020

Related U.S. Application Data

(60) Provisional application No. 62/525,097, filed on Jun. 26, 2017.

(51) Int. Cl.
*A61K 33/18* (2006.01)
*A61K 47/36* (2006.01)

(52) U.S. Cl.
CPC .............. *A61K 33/18* (2013.01); *A61K 47/36* (2013.01)

(58) Field of Classification Search
CPC .................................. A61K 33/18; A61K 47/36
See application file for complete search history.

(56) References Cited

U.S. PATENT DOCUMENTS

| | | | |
|---|---|---|---|
| 2011/0130710 A1* | 6/2011 | Becker | A61P 27/02 604/22 |
| 2012/0184929 A1* | 7/2012 | Davis | A61M 35/006 604/310 |

FOREIGN PATENT DOCUMENTS

WO    WO-2008117300 A2 *  10/2008  ............. A01N 59/12

OTHER PUBLICATIONS

Qing, G. E. N. G. "Effects of iodophor exposure therapy for skin lesion [J]." Journal of Hainan Medical University 9 (2012). (Year: 2012).*

* cited by examiner

*Primary Examiner* — Ali Soroush
(74) *Attorney, Agent, or Firm* — David G. Burleson

(57) ABSTRACT

A topical composition can be used to treat or inhibit onset of fibrillar collagenous growths, including but not limited to keloids. The composition includes elemental iodine carried in a non-migratory vehicle. Application of the composition can result in a significant reduction in the size of such a growth or, if applied to an area of skin susceptible to such a growth, inhibit the onset thereof.

5 Claims, No Drawings

METHOD FOR TREATING FIBRILLAR COLLAGENOUS CONDITIONS

CROSS-REFERENCE TO RELATED APPLICATIONS

This is a national stage entry of international application PCT/US2018/039177 which claims the benefit of U.S. provisional patent application No. 62/525,097, filed 26 Jun. 2017, the disclosure of which is incorporated herein by reference.

BACKGROUND INFORMATION

Human and animal wounds can be classified as (1) acute, which includes skin abrasions, surgical incisions, trauma, burns, acne or chickenpox blisters, bites, piercings, and the like, or (2) chronic, which includes inter alia diabetic ulcers, pressure ulcers, and venous arterial ulcers.

Acute wounds generally heal through an orderly and timely regenerative process with sequential, yet somewhat overlapping, stages of healing: haemostasis, inflammation, and regeneration and repair.

During haemostasis, a damaged endothelial lining exposes platelets to subendothelial collagen. This results in the release of one type of substance that facilitates platelet adhesion to sub-endothelial collagen, with the adhered platelets in turn releasing substances that lead to further platelet aggregation, and another type which then activates the coagulation pathways, leading to the formation of fibrin which permits clotting.

During inflammation, platelets release platelet-derived growth factor and transformation growth factor β, which are chemotactic to neutrophils and monocytes.

In the regeneration-repair phase, the presence of certain growth factors leads to proliferation of epithelial cells and fibroblasts, which produce collagen. A scar forms when fibrillar collagen, either type III (early) or type I (late), locates in the wound bed and permits wound closure. (Early type collagen eventually gets replaced with late-type collagen.)

Certain types of scars, particularly in some racial and ethnic populations, are subject to an overgrowth of collagen in the area of the scar. An overgrowth of granulation tissue (type III collagen) at that site can result in a lump many times larger than the original scar.

Defective wound maturation can manifest as a fibrotic wound, i.e., a wound characterized by excessive formation of collagenous scar tissue, such as hypertrophic scars or keloids, both of which involve excessive accumulations of fibroblasts as well as collagen. The former are elevated scars that typically are restricted to the boundary of the initial injury, while the latter involve excessive fibrous connective tissue and are characterized by a collection of atypical fibroblasts (which proliferate actively) with excessive deposition of extracellular matrix components. Bundles of one of those components, fibrillar collagen, can form nodules in the deep dermal portion of the lesion or nodule.

Common treatment options include corticosteroids such as triamcinolone acetonide, often in combination with additional chemicals, surgical excision, cryosurgery, pressure therapy, laser ablation, and radiation. Many of these are contraindicated for children.

Numerous topical agents have been employed with varying degrees of success in terms of keloid size reduction and recurrence. Examples include vinegar, a mixture of baking soda and hydrogen peroxide, essential oils, acetylsalicylic acid, and halogens, particularly iodine or a mixture of iodine and iodide (Lugol's iodine).

The efficacy of topical treatments often are limited by their ability to remain in contact with the area to be treated.

Simple, safe methods for effectively treating and preventing or inhibiting growth of fibrillar collagenous conditions using a topical composition remain desirable.

SUMMARY

Described herein is a topical composition that can be used both to treat and to inhibit onset of fibrillar collagenous growths including, specifically, keloids. The term "treat" involves reductions in the size (volume) of such a growth including, but not limited to, complete eradication as well as prevention of such growths at the site of breached skin.

In one aspect is provided a method for treating a fibrillar collagenous growth that involves applying thereto a treating composition that includes elemental iodine carried in a nonmigratory vehicle.

In a separate but related aspect is provided a method for inhibiting the onset of a fibrillar collagenous growth that involves applying to breached skin a treating composition that includes elemental iodine carried in a non-migratory vehicle.

Another aspect involves a method for treating a fibrillar collagenous growth in which a human in need thereof is provided with the aforedescribed composition and instructed to apply that composition to the growth or to an area of breached skin.

In yet another aspect is provided a method for treating or inhibiting onset of a fibrillar collagenous growth in which a human in need thereof is provided with a kit that includes the aforedescribed composition and instructions for applying that composition, with the instructions involving application of composition to the growth for treatment purposes or application of composition to breached skin to inhibit onset of such a growth. Such a kit optionally can include a tool for applying the composition to the growth. Also or alternatively, the composition can be provided in a container that assists in metering the composition onto the growth.

In a still further aspect is provided a composition that includes elemental iodine carried in a non-migratory vehicle, with the composition being provided for application to a fibrillar collagenous growth.

In a yet still further aspect is provided a composition that includes elemental iodine carried in a non-migratory vehicle, with the composition being provided for application to an area of breached skin so as to inhibit onset of a fibrillar collagenous growth.

In each of the foregoing aspects, the fibrillar collagenous growth can be a keloid.

To assist in understanding the following description of various embodiments, certain definitions are provided immediately below. These are intended to apply throughout unless the surrounding text explicitly indicates a contrary intention:

"comprising" means including but not limited to those ingredients which follow the term;

"consisting of" means including only those ingredients which follow the term as well as minor amounts of inactive additives or adjuvants;

"consisting essentially of" means including only the listed ingredients, minor amounts (less than 2%, 1%, 0.5%, 0.25%, or 0.1%, all w/v) of other ingredients that supplement the antimicrobial activity and/or provide a secondary effect (e.g., antifogging, soil removal, wound cleaning, etc.) that is desirable in view of the intended end use, and/or inactive additives or adjuvants;

"substituted" (in reference to a functional group) means containing a heteroatom or functionality (e.g., hydrocarbyl group) that does not interfere with the intended purpose of the group in question;

"elemental iodine" means neutral and anionic forms of iodine which include at least two I atoms, including specifically $I_2$ and $I_3^-$;

"iodophor" means a water soluble composition that includes a complex of elemental iodine;

"breached skin" means any wound which compromises the dermis or the healed (closed, scabbed, etc.) area where such a compromise previously occurred;

"dwell time" means the amount of time that a treating composition is allowed to contact a fibrillar collagenous growth or to the area of breached skin;

"non-migratory" means possessing a dynamic viscosity, measured at 25° C. and 5 rpm, of from 200 to 1800 Pa s (200,000 to 1,800,000 cP) using a spindle and a cup of sizes that yield a torque value that is at least 10% of the maximum value measurable by the unit;

"biocompatible" means presenting no significant, long-term deleterious effects on or in a mammalian species.

Hereinthroughout, pH values of a liquid are those which can be obtained from any of a variety of potentiometric techniques employing a properly calibrated electrode, and effective solute concentrations preferably are determined by latent heat of fusion calculations from a properly calibrated DSC unit-produced scan acquired over a temperature range that includes the melting temperature of a given liquid composition.

Any numerical limitation used herein includes an appropriate degree of uncertainty based on the number of significant places used with that particular numerical limitation. For example, "up to 5.0" can be read as setting a lower absolute ceiling than "up to 5."

DETAILED DESCRIPTION

Elemental iodine is a known topical treatment option for fibrillar collagenous growths such as keloids.

Like the other halogens, atomic iodine (I) is one electron short of a full octet, which results in its ability to act as an oxidizing agent. However, its position in the fifth period of the periodic table means that its electronegativity (and, in turn, oxidizing strength) is less than those of halogens in earlier periods.

Both the National Institute for Occupational Safety and Health and the Occupational Safety and Health Administration set 0.1 ppm as, respectively, a recommended exposure limit and the permissible exposure limit for elemental iodine. Exposures at 2 ppm and higher are considered immediately dangerous to health.

Elemental iodine also is a skin irritant, with direct contact capable of causing skin damage. This is true even for elemental iodine-containing solutions, particularly tincture of iodine and Lugol's iodine. Even povidone-iodine trapped against the skin has been reported to cause chemical burns in rare cases.

The following paragraphs describe a composition that includes elemental iodine carried in a non-migratory vehicle, with the composition being provided for application to a fibrillar collagenous growth or to a location susceptible to such a growth, e.g., breached skin.

The treating composition need not contain a large amount of elemental iodine. For example, useful treating compositions include those having an elemental iodine concentration as low as 0.1% (w/w), while concentrations as high as 5% (w/w) also are possible. The maximum permitted concentration of elemental iodine in a treating composition is 10% (w/w) although, advantageously, treating compositions with far less elemental iodine can be quite effective. (Contemplated ranges include combinations of each of the foregoing lower limits with each of the foregoing upper limits.)

Efficacy of the relatively low amount of elemental iodine is enhanced by the ability of the treating compositions to remain in place, which facilitates a large percentage of the elemental iodine in a treating composition being available for contact with a fibrillar collagenous growth. This ability to remain in place results in large part from the elemental iodine being carried in a non-migratory vehicle. The nature of the carrying vehicle assists in permitting delivery of elemental iodine to a fibrillar collagenous growth over an extended period of time.

A non-migratory vehicle can be provided from a variety of ingredients or sources, as long as the targeted characteristics of the overall composition are provided, i.e., ability to convey the desired amount of elemental iodine to the targeted area, ability to remain in place on and/or around the targeted area so that the conveyed elemental iodine can be released over time, biocompatibility, and the like.

A treating composition can be provided by creating a complex of elemental iodine with one or more macromolecules, including polymers and oligomers having the desired physicochemical properties. The treating composition preferably can be characterized as an iodophor.

Formation of a complex typically requires the presence of one or more nucleophilic atoms or functional groups. For example, in povidone-iodine, the N and, more likely, O atoms of the poly(vinylpyrrolidone) are available for complexing with elemental iodine. (In poly(vinylpyrrolidone), a certain percentage of the ketone groups are hypothesized to be in enol or enolate anion form, which are even more likely to be capable of complexing with elemental iodine.) Non-limiting examples of nucleophilic atoms include N, O, S and C, with nucleophilic functional groups being those groups which include such atoms.

A macromolecule with a plurality of such nucleophilic atoms or functional groups can be used as a non-migratory vehicle as long as the macromolecule provides the desired resistance to flow to the treating composition. For example, the viscosity of neat povidone-iodine is too low to permit the treating composition to have the desired dwell time. However, thickening povidone-iodine with a material such as CMC, PVOH, polyacrylamide, gelatin, starch, and the like might provide a carrying vehicle that is sufficiently non-migratory to be useful in the present methods, as long as the effective amount of elemental iodine is kept sufficiently high. (A thickening technique which significantly reduces the effective concentration of elemental iodine in the treating composition and/or forms a barrier through which the elemental iodine must traverse to reach the targeted area, i.e., fibrillar collagenous growth, preferably is avoided.)

Certain modified starches have been found to constitute particularly effective carrying vehicles. Preferred among these are those which are capable of forming iodophors, i.e., those which have good water solubility.

A water soluble modified starch capable of providing a desirable non-migratory vehicle for elemental iodine is 2-hydroxymethylene crosslinked (1-4)-α-D-glucan carboxymethyl ether, typically made by reacting dextrin with epichlorohydrin.

Cadexomer iodine is an iodophor in which 0.9% (w/w) elemental iodine is entrained in a 3-dimensional (primarily) helical matrix of the aforedescribed crosslinked dextrin derivative. It is commercially available in both powder (microbeads) and ointment (blend with PEG and poloxamer) forms under the Iodosorb™ brand (Smith & Nephew).

When applied to a fibrillar collagenous growth or to a location susceptible to such a growth, particularly an area of breached skin, an appropriate treating composition, such as cadexomer iodine, can provide a dwell time of from several hours to several days as long as the composition is not intentionally removed by washing, rubbing, etc. As long as the patient does not exhibit sensitivity to the presence of elemental iodine, the treating composition can be left in place, although the efficacy of an application of treating composition is expected to decrease over time.

Treating composition can be removed with water or a saline solution, often aided by the presences of a surfactant and/or abrading action, such as with a washcloth or other absorbent article.

The aforedescribed methods involving application of a composition that includes elemental iodine carried in a non-migratory vehicle can be used to treat or inhibit onset of any of a variety of fibrillar collagenous growths, including but not limited to keloids. The size of such growths, including keloids, can be visibly reduced, with the volume of such growths being capable of being reduced by at least 25%, 33%, 50%, 67%, 75%, or even more; complete removal can occur with repeated applications over time.

Cadexomer iodine is available over-the-counter in many countries. However, also contemplated are methods of treatment in which a human in need thereof is provided with a treating composition and given instructions regarding application of that composition to a fibrillar collagenous growth. The instructions can involve a single application or a regimen involving multiple applications, optionally alternating with removals.

The treating composition can be provided in a ready-to-apply form or in a form requiring pre-application modification techniques, for example, blending a powder form with a carrying vehicle of appropriate viscosity.

Ready-to-apply forms include any topical dosage form, as defined by the U.S. Food and Drug Administration, which is non-migratory. (Additional information about topical dosage forms can be found in T. Garg et al., "Comprehensive review on additives of topical dosage forms for drug delivery," Drug Deliv., 2015, vol. 22(8), pp. 969-87 (Informa UK Ltd.; London, England), Non-limiting examples include creams, gels, emulsions, lotions, ointments and pastes. In the case of ointments, the base can be oleaginous, absorption, a water-in-oil emulsion, an oil-in-water emulsion, or water soluble (e.g., PEG).

Although not required, a treating composition can be provided as part of a kit that includes instructions for applying that composition to the growth or to a location susceptible to such a growth, particularly breached skin. Such a kit optionally can include a tool for applying the composition to the growth or the vulnerable area. Alternatively or additionally, a kit also optionally can include a material into which an iodophor can be mixed or blended so as to provide an appropriate non-migratory characteristics. Another optional component in such a kit is a container assisting the user to meter an appropriate amount of treating composition onto the growth or to a location susceptible to such a growth.

That which is claimed is:

1. A process for reducing the size of a fibrillar collagenous growth, said fibrillar collagenous growth having an initial volume, said process consisting of (a) providing to a human in need thereof a treating composition that consists of an iodophor carried in a water soluble modified starch that is the reaction product of dextrin and epichlorohydrin and (b) instructing said human to apply said composition to said growth for up to at least two days.

2. The process of claim 1 wherein said iodophor is a macromolecule-thickened povidone-iodine.

3. The process of claim 1 wherein said fibrillar collagenous growth initial volume is reduced by at least 50%.

4. The process of claim 3 wherein said fibrillar collagenous growth initial volume is reduced by at least 67%.

5. The process of claim 4 wherein said fibrillar collagenous growth initial volume is reduced by at least 75%.

* * * * *